United States Patent
Yabe et al.

(10) Patent No.: US 10,531,008 B2
(45) Date of Patent: Jan. 7, 2020

(54) IMAGE PICKUP SYSTEM

(71) Applicant: OLYMPUS CORPORATION, Tokyo (JP)

(72) Inventors: Yusuke Yabe, Chofu (JP); Tomoya Takahashi, Hachioji (JP); Satoshi Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 312 days.

(21) Appl. No.: 15/478,616

(22) Filed: Apr. 4, 2017

(65) Prior Publication Data

US 2017/0208236 A1     Jul. 20, 2017

Related U.S. Application Data

(63) Continuation of application No. PCT/JP2015/076877, filed on Sep. 24, 2015.

(30) Foreign Application Priority Data

Oct. 10, 2014  (JP) ................. 2014-209228

(51) Int. Cl.
*H04N 5/235*     (2006.01)
*A61B 1/00*      (2006.01)
(Continued)

(52) U.S. Cl.
CPC ....... *H04N 5/2353* (2013.01); *A61B 1/00009* (2013.01); *A61B 1/00045* (2013.01);
(Continued)

(58) Field of Classification Search
CPC .............................. A61B 1/045; H04N 5/2353
See application file for complete search history.

(56) References Cited

U.S. PATENT DOCUMENTS

2009/0043162 A1  2/2009  Takahashi
2009/0062617 A1* 3/2009  Mizuyoshi ........... A61B 1/0638
                                                    600/178
(Continued)

FOREIGN PATENT DOCUMENTS

EP      2022388 A1    2/2009
EP      2407087 A2    1/2012
(Continued)

OTHER PUBLICATIONS

International Search Report dated Dec. 22, 2015 issued in PCT/JP2015/076877.
(Continued)

*Primary Examiner* — Rowina J Cattungal
(74) *Attorney, Agent, or Firm* — Scully, Scott, Murphy & Presser, P.C.

(57) ABSTRACT

An image pickup system includes a light source apparatus and a light-source control section performing first control for setting a duty width and perform second control for, after the duty width is set to a minimum duty width by the first control, changing supply timing of the illumination light not to supply the illumination light in a period other than the period where the light amount control by the PWM is permitted and to supply, in the period where the light amount control by the PWM is permitted, light having a light amount integrated value equal to a light amount integrated value supplied in the period other than the period where the light amount control by the PWM is permitted, and an image pickup apparatus, where data representing a driving current value after the change of the supply timing and a value of the pulse width is stored.

4 Claims, 10 Drawing Sheets

(51) Int. Cl.
*A61B 1/05* (2006.01)
*A61B 1/06* (2006.01)
*H04N 5/225* (2006.01)
*H04N 5/378* (2011.01)
*H04N 9/04* (2006.01)

(52) U.S. Cl.
CPC ............ *A61B 1/051* (2013.01); *A61B 1/0676* (2013.01); *A61B 1/0684* (2013.01); *H04N 5/2256* (2013.01); *H04N 5/378* (2013.01); *H04N 5/2351* (2013.01); *H04N 9/045* (2013.01); *H04N 2005/2255* (2013.01)

(56) References Cited

U.S. PATENT DOCUMENTS

| | | | |
|---|---|---|---|
| 2012/0016200 A1 | 1/2012 | Seto et al. | |
| 2012/0016201 A1 | 1/2012 | Seto et al. | |
| 2013/0053642 A1* | 2/2013 | Mizuyoshi | A61B 1/00006 600/109 |
| 2014/0014820 A1* | 1/2014 | Yabe | G02B 23/2469 250/208.1 |
| 2014/0180004 A1* | 6/2014 | Yamashita | A61B 1/0638 600/109 |
| 2014/0203170 A1* | 7/2014 | Ono | G02B 26/02 250/208.1 |

FOREIGN PATENT DOCUMENTS

| | | |
|---|---|---|
| EP | 2407088 A2 | 1/2012 |
| EP | 2 449 951 A1 | 5/2012 |
| EP | 2561798 A1 | 2/2013 |
| JP | 2009-039432 A | 2/2009 |
| JP | 2012-019982 A | 2/2012 |
| JP | 2012-019983 A | 2/2012 |
| JP | 2013-042854 A | 3/2013 |
| JP | 2013-048792 A | 3/2013 |
| JP | 5379932 B1 | 12/2013 |
| JP | 2014-073398 A | 4/2014 |

OTHER PUBLICATIONS

Extended Supplementary European Search Report dated Jul. 9, 2018 in European Patent Application No. 15 84 9328.8.

* cited by examiner

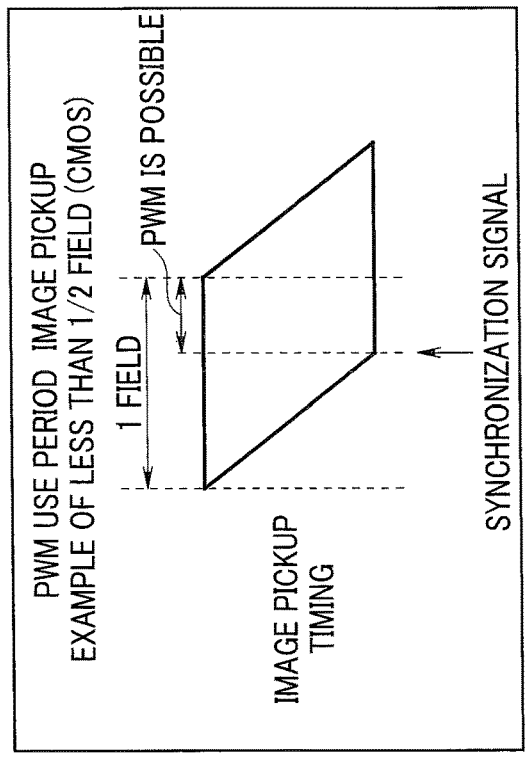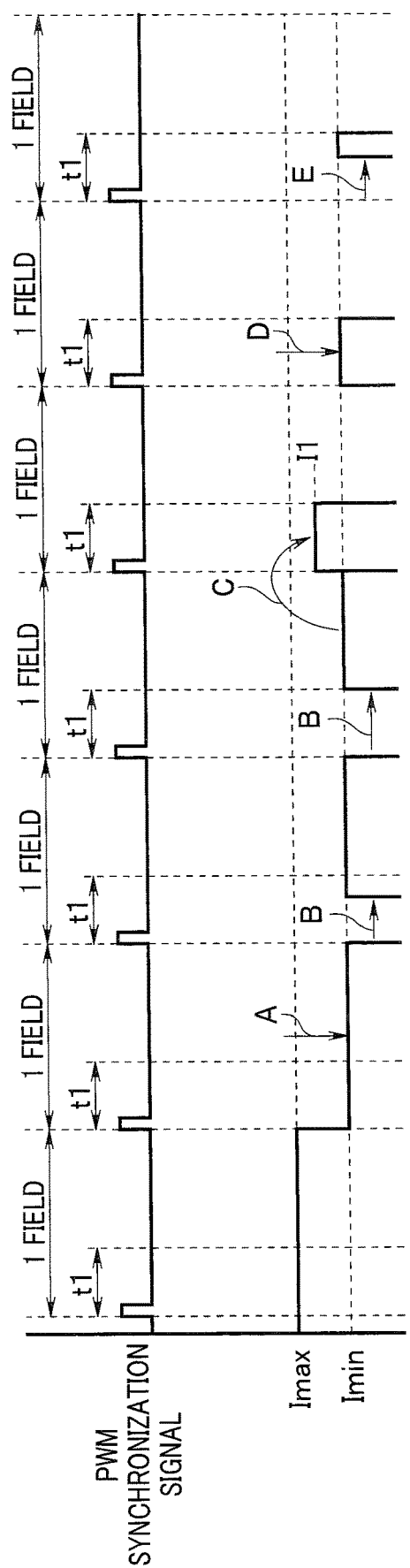

IMAGE PICKUP SYSTEM

CROSS REFERENCE TO RELATED APPLICATION

This application is a continuation application of PCT/JP2015/076877 filed on Sep. 24, 2015 and claims benefit of Japanese Application No. 2014-209228 filed in Japan on Oct. 10, 2014, the entire contents of which are incorporated herein by this reference.

BACKGROUND OF INVENTION

1. Field of the Invention

The present invention relates to an image pickup system.

2. Description of the Related Art

In an image pickup apparatus, a CCD image sensor (hereinafter simply referred to as CCD) has been widely used. However, in recent years, a CMOS image sensor (hereinafter simply referred to as CMOS) has also been widely used. The CMOS has an advantage that the CMOS consumes low power and it is possible to form a peripheral circuit on the same substrate. In a field of an endoscope, an endoscope system in which the CMOS is used has been proposed.

Incidentally, as the CMOS, in general, a rolling shutter scheme in which readout of an image signal is performed in order for each one horizontal line is adopted. In the case of the rolling shutter scheme, a state occurs in which a line under exposure and a line not under exposure are present at the same point in time. When flash light emission is performed in such a point in time, a line on which an object illuminated by illumination light is exposed and a line on which the object is exposed without being illuminated by the illumination light occur. Contrast streaks occur in one screen.

For example, Japanese Patent No. 5379932 discloses an image pickup system in which an image pickup device that sequentially performs exposure for each of horizontal lines is used, the image pickup system being capable of increasing a dynamic range of light adjustment while suppressing contrast streaks of an image.

Further, in such an image pickup system, an optimum light amount control pattern is different depending on a type of an image pickup device mounted on an image pickup apparatus, for example, a CCD or a CMOS. Further, in the CMOS, a period in which PWM light emission can be performed in one field is different depending on a type (the number of lines, a driving frequency, etc.), when the CMOS is mounted on the image pickup apparatus, the optimum light amount control pattern is different depending on a type of the CMOS.

SUMMARY OF THE INVENTION

An image pickup system according to an aspect of the present invention includes: a light source apparatus including: a light source configured to supply illumination light to an object and capable of performing PWM in any duty width; and a light-source control section capable of inputting data of a numerical value indicating a period in which light amount control by the PWM is permitted and configured to perform, on the light source, first control for setting the numerical value of the data to a maximum duty width and setting a duty width between the maximum duty width and minimum duty width and perform second control for, after the duty width is set to the minimum duty width by the first control, changing supply timing of the illumination light not to supply the illumination light to the object in a period other than the period in which the light amount control by the PWM is permitted and to supply, in the period in which the light amount control by the PWM is permitted, light having a light amount integrated value equal to a light amount integrated value supplied in the period other than the period in which the light amount control by the PWM is permitted; an image pickup apparatus provided separately from the light source apparatus, the data of the numerical value indicating the period in which the light amount control by the PWM is permitted being stored in the image pickup apparatus; and a readout section configured to read out the data stored in the image pickup apparatus and set the numerical value of the data to the maximum duty width in the light-source control section. In the image pickup apparatus, data representing a value of a driving current supplied to the light source after the change of the supply timing of the illumination light and a value of the pulse width is further stored.

BRIEF DESCRIPTION OF THE DRAWINGS

FIG. 2A is a diagram for explaining light emission control of an image pickup device (a CMOS), a PWM use period of which is less than a ½ field;

FIG. 2B is a diagram for explaining the light emission control of the image pickup device (the CMOS), the PWM use period of which is less than a ½ field;

DETAILED DESCRIPTION OF THE PREFERRED EMBODIMENT(S)

Embodiments of the present invention are explained below with reference to the drawings.

First Embodiment

Figure 1:
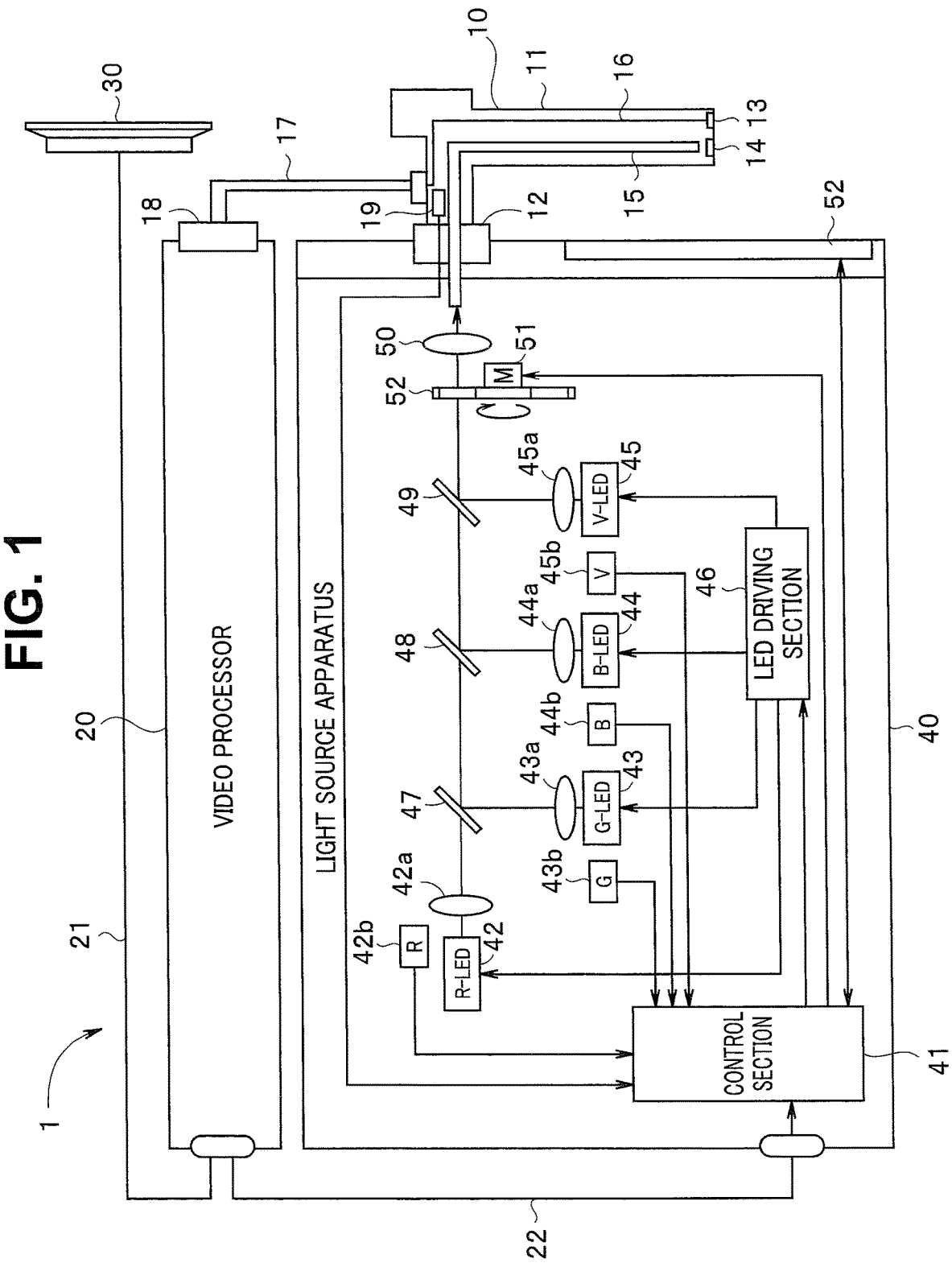
FIG. 1 is a block diagram showing an endoscope system according to a first embodiment.

FIG. 1 is a block diagram showing an endoscope system according to a first embodiment.

In the present embodiment, an endoscope system 1 is explained as an example of an image pickup system. However, the image pickup system is not limited to the endoscope system 1 and can be widely applied to systems including an image pickup function.

The endoscope system 1 is configured by an endoscope 10, a video processor 20, a monitor 30, and a light source apparatus 40. Note that the endoscope system 1 in the present embodiment has a configuration in which the video processor 20 and the light source apparatus 40 are separated. However, the endoscope system 1 may have a configuration in which the video processor 20 and the light source apparatus 40 are integrated.

The endoscope 10 functioning as an image pickup apparatus includes, on a distal end side, an elongated insertion section 11 insertable into a lumen or the like. A proximal end side of the endoscope 10 is detachably connected to the light source apparatus 40 by a connector 12. The endoscope 10 is detachably connected to the video processor 20 by a cable 17 and a connector 18. In this way, endoscopes of different types can be attached to the light source apparatus 40 and the video processor 20.

At a distal end of the insertion section 11, an image pickup device 13 for picking up a video of an object such as an inside of a lumen and a lens 14 for radiating light emitted from the light source apparatus 40 on the object are disposed. Illumination light transmitted from the light source apparatus 40 via a light guide 15 is radiated on the object by the lens 14. The image pickup device 13 is configured by a CCD or CMOS sensor or the like. Return light from the object is made incident on an image pickup surface. The image pickup device 13 photoelectrically converts an incident object optical image and sequentially outputs image pickup outputs based on accumulated charges.

The image pickup device 13 operates with a driving signal including a synchronization signal supplied from the video processor 20 to the image pickup device 13. The image pickup device 13 supplies an image pickup output to the video processor 20 via a signal line 16.

Note that the image pickup device 13 has a predetermined spectral sensitivity characteristic. A characteristic of a picked-up image changes for each of endoscopes mainly because of an influence of a spectral sensitivity characteristic of an image pickup device. In the endoscope 10, a storing section 19 having stored therein scope information including information such as a spectral sensitivity characteristic for each of the endoscopes is provided. By connecting the endoscope 10 to the light source apparatus 40 with the connector 12, it is possible to acquire, in the light source apparatus 40, the scope information stored in the storing section 19.

The video processor 20 applies predetermined signal processing to the image pickup output to generate a video signal that can be displayed on the monitor 30. The video signal from the video processor 20 is supplied to the monitor 30 via a cable 21. In this way, an endoscopic image based on the image pickup output can be displayed on a display screen of the monitor 30.

The video processor 20 can control the light source apparatus 40 to set brightness of the picked-up image to target brightness. The video processor 20 outputs information concerning a ratio of the brightness obtained from the picked-up image and the target brightness to the light source apparatus 40 as brightness control information. The brightness control information is supplied to a control section 41 of the light source apparatus 40 via a cable 22.

The light source apparatus 40 includes an LED (R-LED) 42 configured to generate red light, an LED (G-LED) 43 configured to generate green light, an LED (B-LED) 44 configured to generate blue light, and an LED (V-LED) 45 configured to generate violet light. In this way, the LEDs 42 to 45 configuring a plurality of semiconductor light emitting devices respectively emit illumination lights of different colors for illuminating the object. Note that, in the present embodiment, an example is explained in which four LEDs 42 to 45 configured to generate lights of four colors are adopted. However, kinds of colors and the number of colors are not limited to the present embodiment. In the present embodiment, a configuration may be adopted in which only one LED configured to generate white light is used or a configuration may be adopted in which an LED configured to generate amber light is added to FIG. 1.

Lenses 42a to 45a are respectively disposed on optical axes of the emitted lights of the respective LEDs 42 to 45. The respective lenses 42a to 45a respectively convert the emitted lights of the LEDs 42 to 45 into substantially parallel lights and emit the substantially parallel lights. Dichroic filters 47 to 49 are disposed on an optical axis of the lens 42a configured to emit light emitted from the R-LED 42. Light emitted from the G-LED 43 is also made incident on the dichroic filter 47 via the lens 43a. Light emitted from the B-LED 44 is also made incident on the dichroic filter 48 via the lens 44a. Light emitted from the V-LED 45 is also made incident on the dichroic filter 49 via the lens 45a.

The dichroic filter 47 reflects the light emitted from the G-LED 43 and transmits the light emitted from the R-LED 42. Similarly, the dichroic filter 48 reflects the light emitted from the B-LED 44 and transmits the transmitted light of the dichroic filter 47. Similarly, the dichroic filter 49 reflects the light emitted from the V-LED 45 and transmits the transmitted light of the dichroic filter 48.

In this way, the lights of the LEDs 42 to 45 are combined by the dichroic filters 47 to 49. Combined light from the dichroic filter 49 is made incident on the light guide 15 via a lens 50. Note that disposition order of the LEDs 42 to 45 can also be changed by setting characteristics of the dichroic filters 47 to 49 as appropriate. However, it is easier to set the characteristics of the dichroic filters when the LEDs 42 to 45 are disposed in order of wavelength bands of the emitted lights of the LEDs 42 to 45.

A rotating filter 52 driven to rotate by a motor 51 is provided between the dichroic filter 49 and the lens 50. The rotating filter 52 includes an opening used in a normal observation mode, an NBI filter used in a narrow band observation (NBI) mode, and the like. The motor 51 is controlled according to a control signal from the control section 41 to drive to rotate the rotating filter 52. Consequently, the opening, the NBI filter, or the like of the rotating filter 52 is disposed on an optical path of the combined light from the dichroic filter 49. Switching of an observation mode is performed.

The respective LEDs 42 to 45 are driven to be lit by an LED driving section 46. The LED driving section 46 configuring a light-emitting-device driving section is controlled by the control section 41 to generate PWM pulses, which are driving signals for driving the respective LEDs 42 to 45. Note that the respective LEDs 42 to 45 emit lights with light emission amounts corresponding to duty ratios and current amounts of the PWM pulses received from the LED driving section 46. The control section 41 outputs light adjustment information for controlling the respective LEDs 42 to 45 to the LED driving section 46 to control the duty ratios and current levels of the PWM pulses and performs light adjustment control of the respective LEDs 42 to 45.

Optical sensors 42b to 45b are disposed in positions where emitted lights of the respective LEDs 42 to 45 can be detected. The respective optical sensors 42b to 45b configuring a plurality of light detecting sections respectively detect illuminance values of illumination lights of respective colors of the respective LEDs 42 to 45 and output detection results to the control section 41. Note that the respective optical sensors 42b to 45b are disposed in positions other than positions on optical paths leading from the respective LEDs 42 to 45 to the lenses 42a to 45a.

The control section 41 generates light adjustment information such that light emission amounts of the respective LEDs 42 to 45 can maintain a predetermined color balance. A color balance of the respective LEDs 42 to 45 needs to be determined according to a spectral sensitivity characteristic of the endoscope 10.

The control section 41 controls, on the basis of the brightness control information supplied from the video processor 20, light amounts of the respective LEDs 42 to 45 while maintaining a ratio of the light emission amounts (a light amount ratio) of the respective LEDs 42 to 45 such that an optimum color balance can be obtained. For example, the control section 41 calculates light adjustment information corresponding to a light amount value of the G-LED 43 that should be set according to the brightness control information supplied from the video processor 20 and, concerning the other LEDs 42, 44, and 45, according to the light amount value of the G-LED 43, calculates light adjustment information such that a color amount ratio is a predetermined light amount ratio.

More specifically, the control section 41 performs light emission control (PWM control and current control) on the G-LED 43 on the basis of the brightness control information supplied from the video processor 20. The light emission control is performed by the control section 41 reading out the scope information stored in the storing section 19 of the endoscope 10. The scope information is information concerning control parameters and a target color balance ratio. The control section 41 performs the light emission control of the G-LED 43 using the control parameters (a PWM use period, a current after area translation, and a PWM width after area translation). Note that the light emission control of the G-LED 43 is explained below.

The control section 41 performs the light emission control on the other LEDs 42, 44, and 45 using a PWM pulse (light emission timing) common to the G-LED 43. Concerning the other LEDs 42, 44, and 45, the control section 41 controls light amount values on the basis of a detection result of the optical sensor 43b of the G-LED 43 and a detection result of the optical sensor 42b, 44b, or 45b of the color of the LED such that a color balance ratio reaches the target color balance ratio stored in the storing section 19 (i.e., such that a light amount ratio to the G-LED 43 is a target ratio).

The light emission control of the G-LED 43 of the endoscope system 1 configured in this way is explained. In the present embodiment, light emission control shown in FIG. 2A to FIG. 5B is performed according to a type of the image pickup device 13 mounted on the endoscope 10.

FIG. 2A and FIG. 2B are diagrams for explaining light emission control of an image pickup device (a CMOS), a PWM use period of which is less than a ½ field.

The image pickup device 13 mounted on the endoscope 10 is a CMOS, image pickup timing, that is, a PWM use period of which is less than a ½ field, shown in FIG. 2A.

The control section 41 functioning as a readout section reads out the control parameters (the PWM use period, the current after area translation, and the PWM width after area translation) of the scope information from the storing section 19 of the endoscope 10. The control section 41 functioning as a parameter setting section sets the control parameters read out from the storing section 19 as control parameters used in a predetermined control sequence. The control section 41 functioning as a light-source control section controls an emission form of illumination light from the G-LED 43 on the basis of the predetermined control sequence.

Note that the control parameters stored in the storing section 19 are not limited to the PWM use period, the current after area translation, and the PWM width after area translation and may include, for example, parameters used in various kinds of signal processing in the video processor 20. On behalf of the control section 41 of the light source apparatus 40, the video processor 20 performs the readout of the control parameters stored in the storing section 19 via the cable 17 and the connector 18. In this case, among the control parameters read out from the storing section 19, the video processor 20 only has to set parameters used in the video processor 20 in a not-shown signal processing circuit in the video processor 20 and output parameters used in the light source apparatus 40 to the control section 41 of the light source apparatus 40 via the cable 22.

The control parameters read out from the storing section 19 include at least the PWM use period, the current after area translation, and the PWM width after area translation. The PWM use period is PWM control period length data representing a length of a period in which control by the control section 41 is carried out within an image pickup period of one frame in the endoscope 10. The current after area translation is data representing a value of a driving current supplied to the G-LED 43 after a change of the emission timing of the illumination light. Further, the PWM width after area translation is data representing a value of pulse width supplied to the G-LED 43 after the change of the emission timing of the illumination light.

As the control parameters stored in the storing section 19, the PWM use period is t1 ms (less than a ½ field), the current after area translation is I1 A, and the PWM width after area translation is t1 ms.

The control section 41 executes the predetermined control sequence as explained below and controls a light amount of the G-LED 43 on the basis of the control parameters. First, as shown in FIG. 2B, the control section 41 reduces an electric current from a maximum current (Imax A) to a minimum current (Imin A) in all bands (an arrow A).

Subsequently, the control section 41 narrows down a Duty width of PWM in the PWM use period to a minimum value (an arrow B). Subsequently, the control section 41 performs area translation from a PWM nonuse period to the PWM use period on the basis of information of the current after area translation (I1 A) and the PWM width after area translation (t1 ms) (an arrow C).

Subsequently, the control section 41 reduces the electric current to the minimum current (Imin A) in the PWM use period (an arrow D). Finally, the control section 41 narrows down the Duty width of PWM in the PWM use period to the minimum value (an arrow E) and ends the light emission control of the G-LED 43.

Concerning the other LEDs 42, 44, and 45, as explained above, the control section 41 controls the light amount values on the basis of the detection result of the optical sensor 43*b* of the G-LED 43 and the detection results of the optical sensor 42*b*, 44*b*, or 45*b* of the color of the LED such that a color balance ratio reaches the target color balance ratio stored in the storing section 19. That is, the control section 41 controls light emission patterns of the other LEDs 42, 44, and 45 to follow the one G-LED 43. In FIG. 3A to FIG. 5B referred to below, control of the light amount values of the other LEDs 42, 44, and 45 is the same.

Figure 3A:
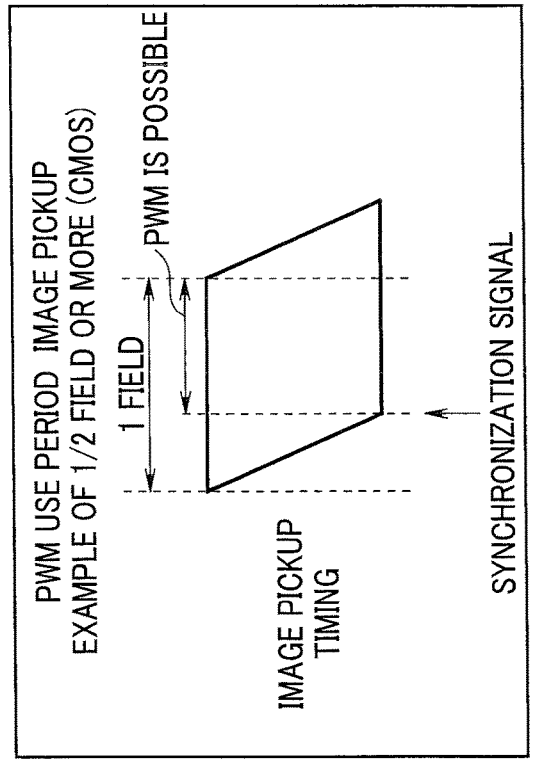
FIG. 3A is a diagram for explaining light emission control of an image pickup device (a CMOS), a PWM use period of which is a ½ field or more.
Figure 3B:
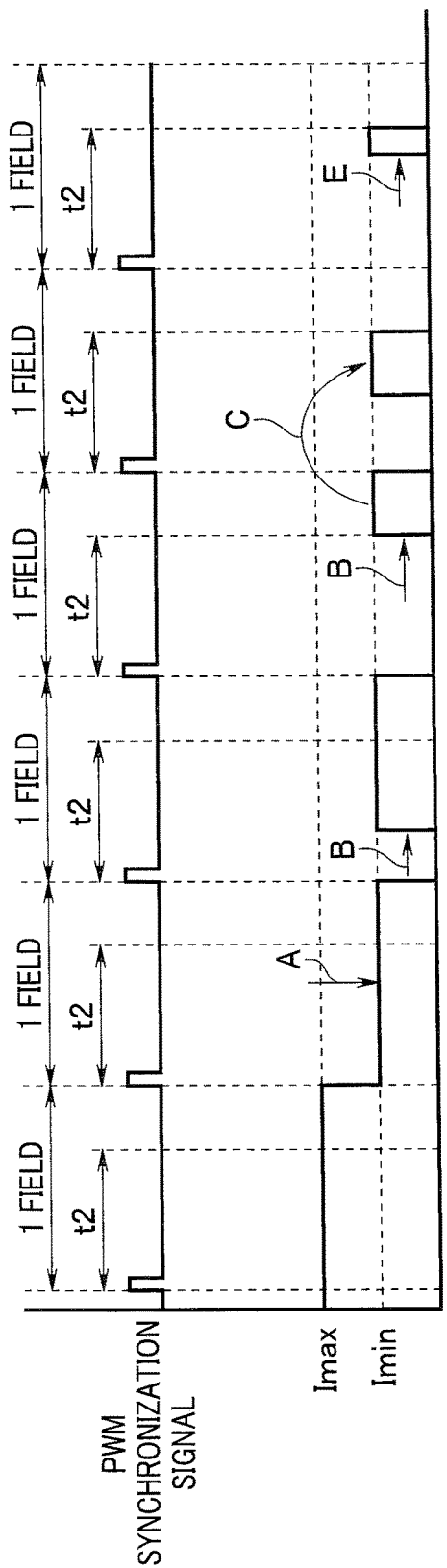
FIG. 3B is a diagram for explaining the light emission control of the image pickup device (the CMOS), the PWM use period of which is a ½ field or more.

FIG. 3A and FIG. 3B are diagrams for explaining light emission control of an image pickup device (a CMOS), a PWM use period of which is a ½ field or more.

The image pickup device 13 mounted on the endoscope 10 is a CMOS, image pickup timing, that is, a PWM use period of which is a ½ field or more, shown in FIG. 3A.

As the control parameters stored in the storing section 19, the PWM use period is t2 ms (a ½ field or more), the current after area translation is Imin A, and the PWM width after area translation is one field—t2 ms.

The control section 41 executes the predetermined control sequence as explained below and controls the light amount of the G-LED 43 on the basis of the control parameters. First, as shown in FIG. 3B, the control section 41 reduces an electric current from a maximum current (Imax A) to a minimum current (Imin A) in all bands on the basis of the control parameters (an arrow A). Subsequently, the control section 41 narrows down a Duty width of PWM in the PWM use period to a minimum value (an arrow B). Subsequently, the control section 41 performs area translation from a PWM nonuse period to the PWM use period on the basis of information of the current after area translation (Imin A) and the PWM width after area translation (one field—t2 ms) (an arrow C).

In an example shown in FIG. 3A and FIG. 3B, the PWM use period is longer than the PWM nonuse period. Therefore, the current after area translation remains at the minimum current (Imin A). Therefore, the processing indicated by the arrow D in FIG. 2B is omitted. Finally, the control section 41 narrows down the Duty width of PWM to a minimum value in the PWM use period (an arrow E) and ends the light emission control of the G-LED 43.

Figure 4A:
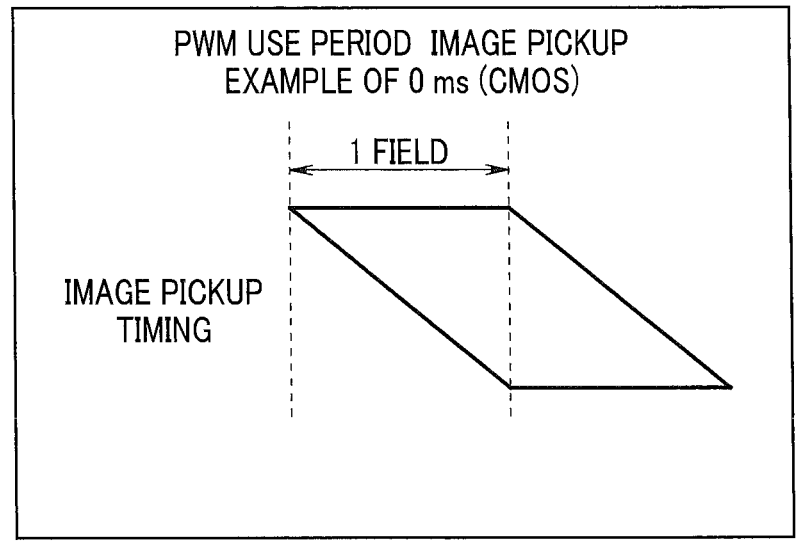
FIG. 4A is a diagram for explaining light emission control of an image pickup device (a CMOS), a PWM use period of which is 0 ms.
Figure 4B:
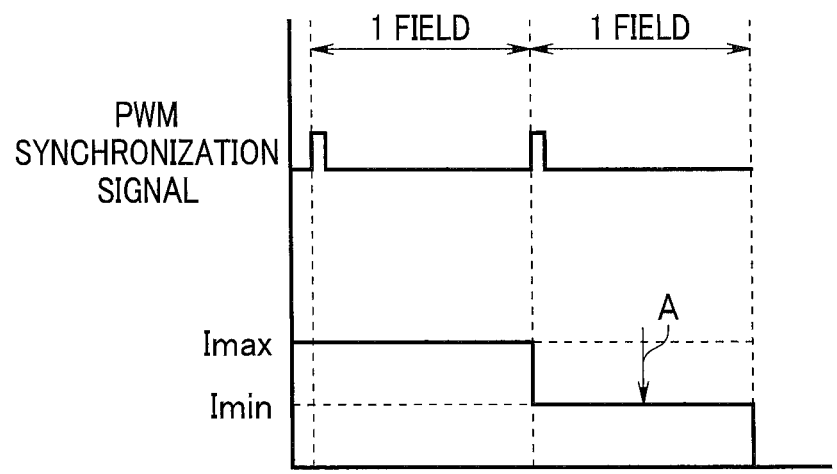
FIG. 4B is a diagram for explaining the light emission control of the image pickup device (the CMOS), the PWM use period of which is 0 ms.

FIG. 4A and FIG. 4B are diagrams for explaining light emission control of an image pickup device (a CMOS), a PWM use period of which is 0 ms.

The image pickup device 13 mounted on the endoscope 10 is a CMOS, image pickup timing, that is, the PWM use period of which is absent, shown in FIG. 4A.

As the control parameters, the PWM use period is 0 ms, the current after area translation is 0 A, and the PWM after area translation is 0 ms.

The control section 41 executes the predetermined control sequence as explained below and controls the light amount of the G-LED 43 on the basis of the control parameters. First, as shown in FIG. 4B, the control section 41 reduces an electric current from a maximum current (Imax A) to a minimum current (Imin A) in all bands on the basis of the control parameters (an arrow A) and ends the light emission control of the G-LED 43. In an example shown in FIG. 4A and FIG. 4B, since the image pickup device does not have the PWM use period, the processing of the narrow down of the Duty width of PWM indicated by an arrow B in FIG. 2B and the subsequent processing cannot be performed. Therefore, the current after area translation is 0 A and the PWM after area translation is 0 ms. Only the narrow down of the electric current (the arrow A) is performed.

Figure 5A:
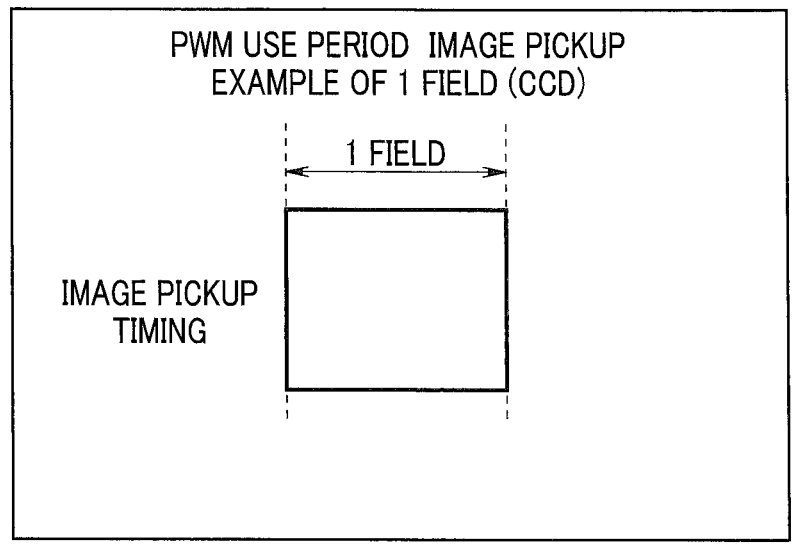
FIG. 5A is a diagram for explaining light emission control of an image pickup device (a CCD), a PWM use period of which is one field.
Figure 5B:
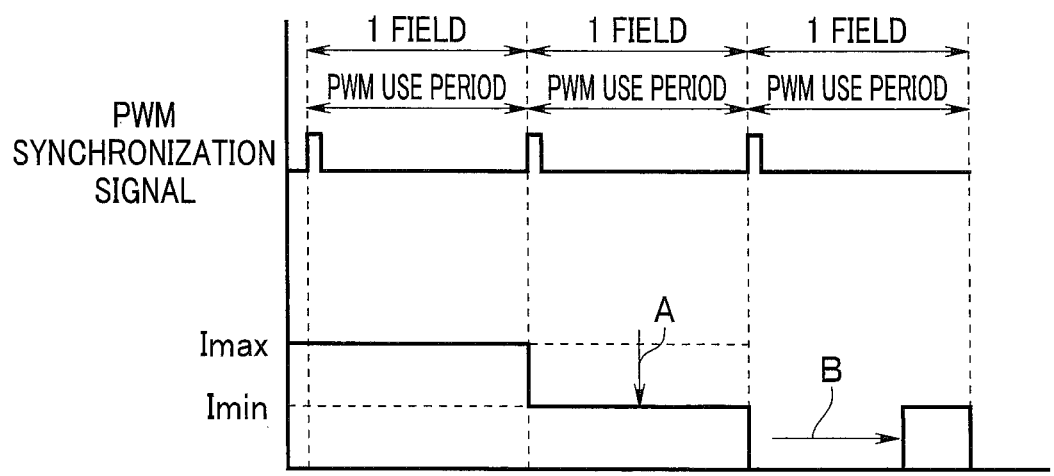
FIG. 5B is a diagram for explaining the light emission control of the image pickup device (the CCD), the PWM use period of which is one field.

FIG. 5A and FIG. 5B are diagrams for explaining light emission control of an image pickup device (a CCD), a PWM use period of which is one field.

The image pickup device 13 mounted on the endoscope 10 is a CCD, image pickup timing, that is, a PWM use period of which is one field, shown in FIG. 5A.

As the control parameters, the PWM use period is one field, the current after area translation is 0 A, and the PWM width after area translation is 0 ms.

The control section 41 executes the predetermined control sequence as explained below and controls the light amount of the G-LED 43 on the basis of the control parameters. First, as shown in FIG. 5B, the control section 41 reduces an electric current from a maximum current (Imax A) to a minimum current (Imin A) in all bands on the basis of the control parameters (an arrow A). Finally, the control section 41 narrows down the Duty width of PWM to a minimum value in the PWM use period (an arrow B) and ends the light emission control of the G-LED 43.

When the image pickup device 13 is a CCD, since the PWM use period is one field, it is unnecessary to perform the processing of the area translation indicated by the arrow C in FIG. 2B and the subsequent processing. Therefore, the current after area translation is 0 A and the PWM width after area translation is 0 ms. The narrow down of the electric current (the arrow A) and the narrow down of the Duty width of PWM (the arrow B) are performed.

As explained above, in the endoscope system 1, the control parameters corresponding to the type of the image pickup device 13 mounted on the endoscope 10 are stored in the storing section 19. The endoscope system 1 performs the light emission control of the G-LED 43 according to the control parameters. As a result, the endoscope system 1 is capable of performing light amount control in an optimum dynamic range according to the image pickup device 13 mounted on the endoscope 10.

Therefore, with the endoscope system 1, which is the image pickup system in the present embodiment, it is possible to appropriately control a light amount of illumination light in a wide dynamic range according to a type of the image pickup device mounted on the image pickup apparatus.

Second Embodiment

A second embodiment is explained.

Figure 6:
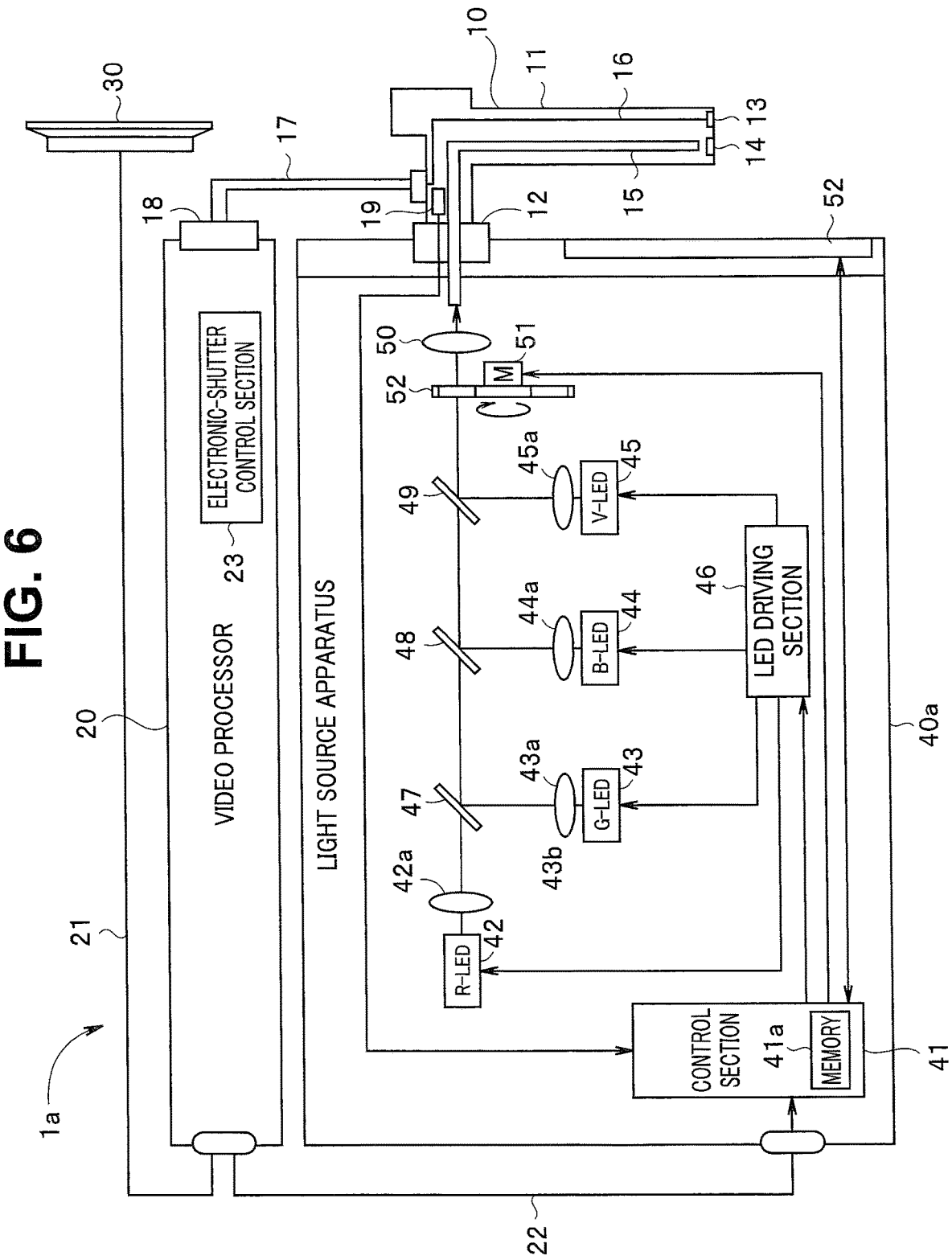
FIG. 6 is a block diagram showing an endoscope system according to a second embodiment.

FIG. 6 is a block diagram showing an endoscope system according to the second embodiment. Note that, in FIG. 6, components same as the components shown in FIG. 1 are denoted by the same reference numerals and signs and explanation of the components is omitted.

As shown in FIG. 6, an endoscope system 1*a* is configured by deleting the optical sensors 42*b* to 45*b* from the endoscope system 1 shown in FIG. 1. The control section 41 includes a memory 41a. Further, the video processor 20 of the endoscope system 1a includes an electronic-shutter control section 23.

In the memory 41a, light emission information, which is rising time periods/falling time periods of light emission of the respective LEDs 42 to 45, is stored. The control section 41 controls a Duty width of PWM of the respective LEDs 42 to 45 on the basis of the light emission information stored in the memory 41a.

When the image pickup device 13 is a CCD having an electronic shutter function, the electronic-shutter control section 23 controls an electronic shutter according to control by the control section 41.

Figure 7A:
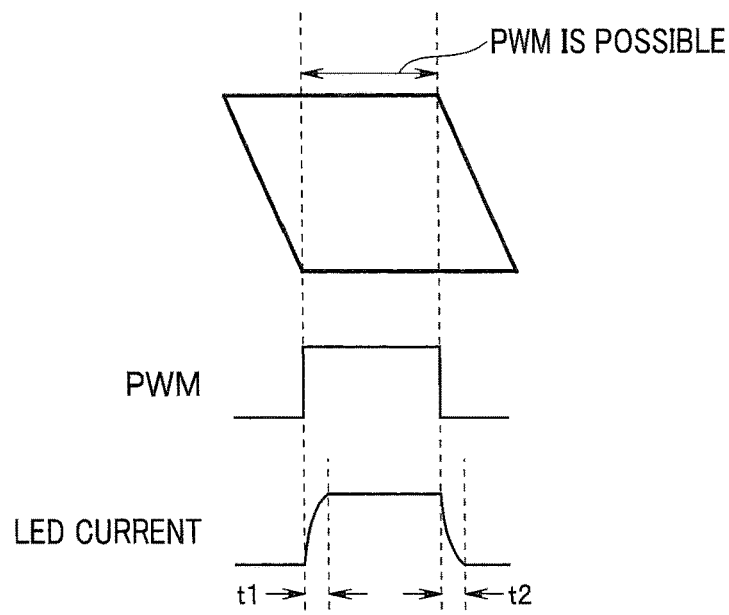
FIG. 7A is a diagram showing light emission timing in the case in which an image pickup device is a CMOS.
Figure 7B:
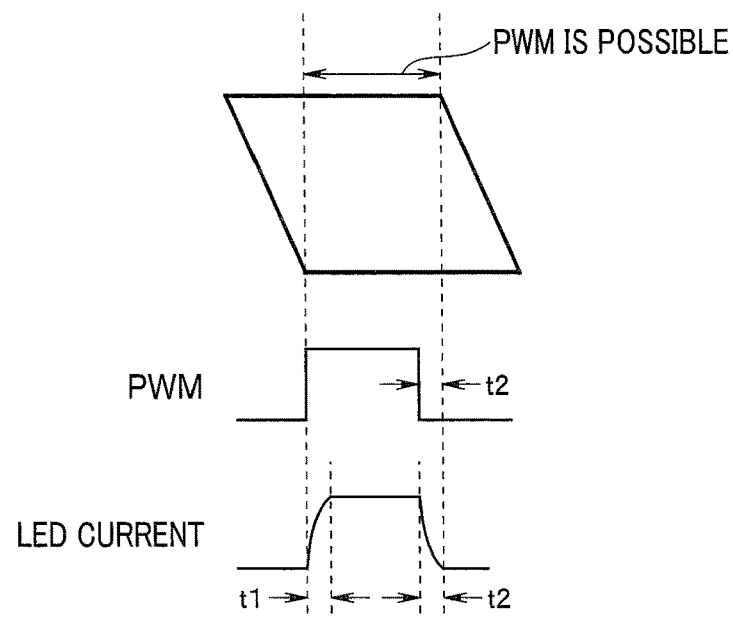
FIG. 7B is a diagram showing the light emission timing in the case in which the image pickup device is the CMOS.

First, light emission timing in the case in which the image pickup device 13 is a CMOS is explained. FIG. 7A and FIG. 7B are diagrams showing light emission timing in the case in which the image pickup device is a CMOS.

As shown in FIG. 7A, when PWM is performed in a PWM usable period, an LED current flows in a period other than the PWM usable period because of a falling time period t2 and color unevenness occurs.

Therefore, the control section 41 corrects extinction start timing of an LED on the basis of the falling time period t2 of the light emission information stored in the memory 41a. More specifically, as shown in FIG. 7B, the control section 41 reduces the PWM by the falling time period t2 and ends the PWM.

Note that the optical sensors 42b to 45b shown in FIG. 1 may be provided in a light source apparatus 40a. Rising time periods/falling time periods of light emission of the respective LEDs 42 to 45 may be detected on the basis of detection signals of the optical sensors 42b to 45b. In this case, even if the light emission information is not stored in the memory 41a in advance, it is possible to perform the PWM control.

Consequently, in the endoscope system 1a, since the respective LEDs 42 to 45 emit lights only in the PWM usable time of the CMOS, it is possible to prevent occurrence of color unevenness.

Figure 8:
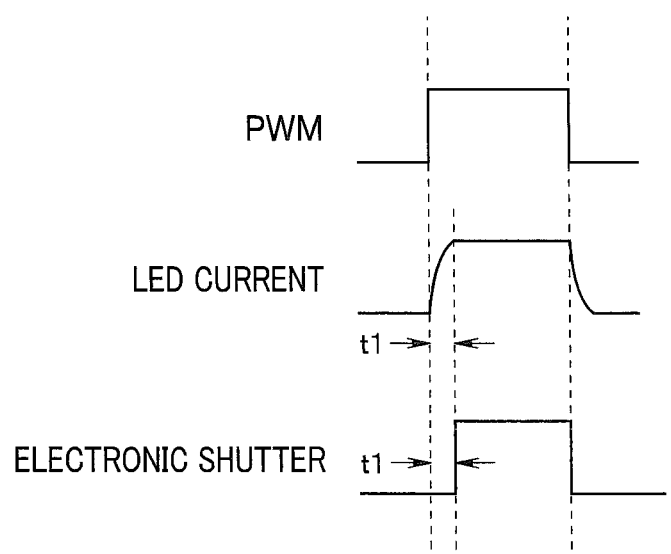
FIG. 8 is a diagram showing light emission timing and shutter timing in the case in which the image pickup device is a CCD.

Light emission timing and shutter timing in the case in which the image pickup device 13 is a CCD having an electronic shutter function are explained. FIG. 8 is a diagram showing light emission timing and shutter timing in the case in which the image pickup device is a CCD.

The control section 41 detects, on the basis of a rising time period t1 of light emission information, shutter timing when exposure timing of an electronic shutter is started in a period in which light emission by the PWM is stable and sets the shutter timing in the electronic-shutter control section 23.

The electronic-shutter control section 23 controls the electronic shutter on the basis of the shutter timing received from the control section 41. Consequently, as shown in FIG. 8, the electronic shutter operates with a delay of the rising time period t1 from the start of the PWM.

Note that, as in the CMOS explained above, the optical sensors 42b to 45b shown in FIG. 1 may be provided in the light source apparatus 40a. Rising time periods/falling time periods of light emission of the respective LEDs 42 to 45 may be detected on the basis of detection signals of the optical sensors 42b to 45b. In this case, it is possible to perform the above electronic shutter control even if light emission information is not stored in the memory 41a in advance.

Consequently, the endoscope system 1a can associate light adjustment by the electronic shutter with a period in which the light emission by the PWM is stable. It is possible to perform the light adjustment in a state in which a color balance is maintained.

Third Embodiment

A third embodiment is explained.

The light source apparatus 40 shown in FIG. 1 includes the plurality of LEDs 42 to 45, the LED driving section 46 configured to generate driving currents for the LEDs 42 to 45, and the optical sensors 42b to 45b configured to detect light emission states of the respective LEDs 42 to 45. The light source apparatus 40 secures a light amount and a color balance necessary for illumination light by appropriately adjusting current amounts fed to the respective LEDs 42 to 45. Light amounts of the LEDs 42 to 45 are adjusted by the PWM control of electric currents. It is necessary to connect the LEDs 42 to 45 and the LED driving section 46 with low resistance in order to secure a waveform of the PWM. Therefore, the LED driving section 46 is disposed near the LEDs 42 to 45.

The optical sensors 42b to 45b configured to detect light emission states of the LEDs 42 to 45 are disposed near the LEDs 42 to 45 in order to detect lights of the LEDs 42 to 45. Consequently, in general, the optical sensors 42b to 45b and the LED driving section 46 are disposed adjacent to the same substrate. Therefore, when large currents are inputted to the LEDs 42 to 45, since a heat generating device of the LED driving section 46 is heated, the optical sensors 42b to 45b adjacent to the LED driving section 46 are also heated. As a result, accuracy of light detection of the LEDs 42 to 45 may be deteriorated.

Therefore, in the third embodiment, a light source apparatus that can keep optical sensors at a constant temperature or less and secure an appropriate light emission state of a light source even when LEDs are driven by large currents is explained.

Figure 9A:
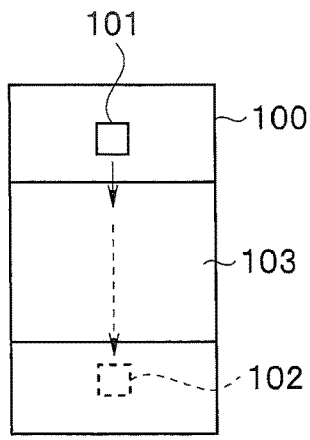
FIG. 9A is a diagram for explaining an example of a substrate including an LED driving section and an optical sensor.
Figure 9B:
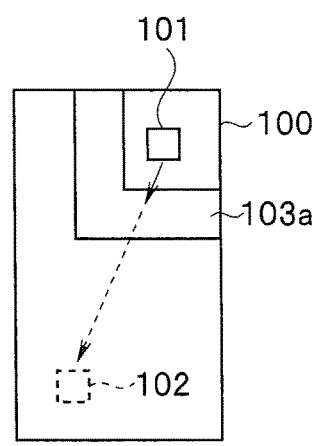
FIG. 9B is a diagram for explaining the example of the substrate including the LED driving section and the optical sensor.
Figure 9C:
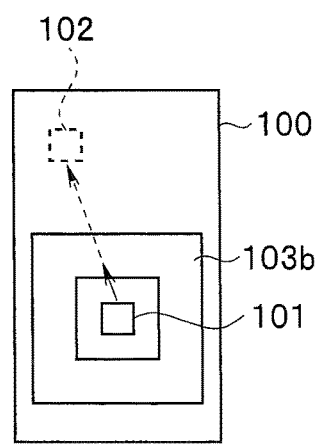
FIG. 9C is a diagram for explaining the example of the substrate including the LED driving section and the optical sensor.

FIG. 9A, FIG. 9B, and FIG. 9C are diagrams for explaining an example of a substrate including an LED driving section and an optical sensor.

As shown in FIG. 9A, an LED driving section 101 and an optical sensor 102 are disposed on a substrate 100. Note that the LED driving section 101 and the optical sensor 102 are disposed on an upper surface and a lower surface of the substrate 100. However, the LED driving section 101 and the optical sensor 102 are not limited to this and may be disposed on the same surface.

On the surface of the substrate 100, a GND layer 103 formed of, for example, copper foil is provided between the LED driving section 101 and the optical sensor 102 to traverse all heat conduction routes. Consequently, heat from the LED driving section 101 is radiated from the GND layer 103 on the surface of the substrate 100 to atmosphere to keep temperature of the optical sensor 102 at a constant temperature or less.

Note that a shape of the GND layer 103 is not limited to that shown in FIG. 9A. For example, as shown in FIG. 9B, an L-shaped GND layer 103a may be provided to surround the LED driving section 101. As shown in FIG. 9C, a GND layer 103b having a hollow square shape may be provided to surround the LED driving section 101.

Figure 10A:
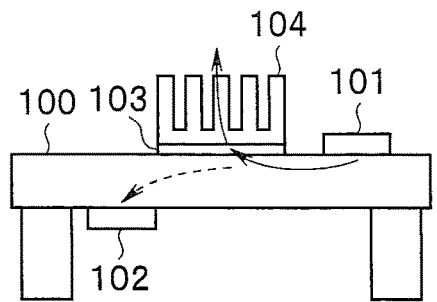
FIG. 10A is a diagram for explaining another example of the substrate including the LED driving section and the optical sensor.
Figure 10B:
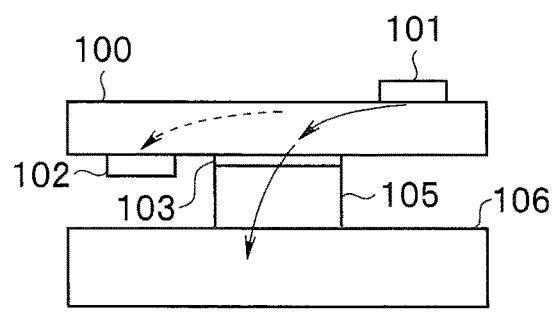
FIG. 10B is a diagram for explaining still another example of the substrate including the LED driving section and the optical sensor.
Figure 10C:
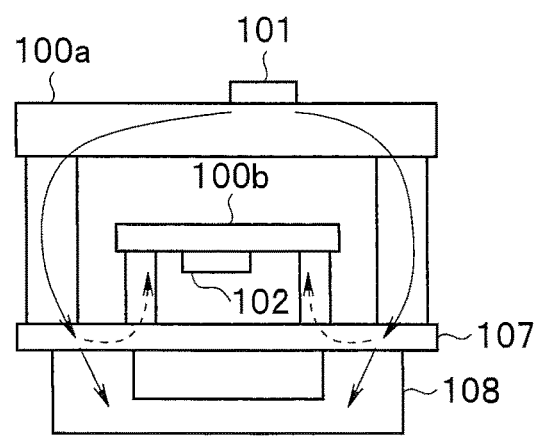
FIG. 10C is a diagram for explaining still another example of the substrate including the LED driving section and the optical sensor.

FIG. 10A, FIG. 10B, and FIG. 10C are diagrams for explaining another example of the substrate including the LED driving section and the optical sensor.

As shown in FIG. 10A, a heat diffusing member 104 formed of a heat sink or the like may be provided in contact with the GND layer 103 on the surface of the substrate 100 to radiate heat generated in the LED driving section 101 to the atmosphere.

As shown in FIG. 10B, a heat conduction member 105 may be provided in contact with the GND layer 103 on the surface of the substrate 100 and a housing exterior 106 formed of metal or the like may be provided in contact with the heat conduction member 105 to radiate heat generated in the LED driving section 101 to a member around the LED driving section 101.

As shown in FIG. 10C, the LED driving section 101 and the optical sensor 102 may be disposed on different substrates. That is, the LED driving section 101 is disposed on a substrate 100a, the optical sensor 102 is disposed on a substrate 100b, and a heat conduction member 107 functioning as a heat route among all heat conduction routes from the LED driving section 101 to the optical sensor 102 is provided. The heat conduction member 107 is set in contact with a peripheral member 108 formed of metal or the like to radiate heat generated in the LED driving section 101 to the peripheral member 108.

As explained above, the heat generating device of the LED driving section 101 disposed near the LEDs and the optical sensor 102 are thermally shielded. It is possible to keep the temperature of the optical sensor 102 at the constant temperature or less even when the LEDs are driven with large currents. Consequently, it is possible to more accurately detect light emission amounts of the LEDs with the optical sensor 102. It is possible to keep the light emission amounts of the LEDs generated by the PWM control in an appropriate light emission state.

Note that, besides the embodiments, a PWM use period may be controlled on the basis of ON/OFF of the electronic shutter.

More specifically, in the video processor 20, an automatic light adjustment mode for determining ON/OFF of the electronic shutter on the basis of the scope information stored in the storing section 19 of the endoscope 10 and a manual mode for controlling ON/OFF of the electronic shutter according to operation by the user may be selectable.

For example, selection of the automatic light adjustment mode and the manual mode is performed by a mode selection switch provided in the light source apparatus 40.

When the automatic light adjustment mode is selected, the video processor 20 determines ON/OFF of the electronic shutter on the basis of the scope information stored in the storing section 19 in the endoscope 10. When the electronic shutter is turned on, the control section 41 of the light source apparatus 40 fixes the PWM use period to one field, changes only driving current values of various light sources such as LEDs and LDs (laser diodes), and controls light amounts. On the other hand, when the electronic shutter is turned off by the video processor 20, the control section 41 of the light source apparatus 40 controls both of PWM duties and driving current values of the various light sources.

On the other hand, when the manual mode is selected and the electronic shutter is turned on according to the operation by the user, the control section 41 of the light source apparatus 40 fixes the PWM use period to one field, changes only driving current values of the various light sources, and controls light amounts. On the other hand, when the electronic shutter is turned off according to the operation by the user, the control section 41 of the light source apparatus 40 controls both of the PWM duties and the driving current values of the various light sources.

The present invention is not limited to the embodiments explained above. Various changes, alterations, and the like are possible in a range in which the gist of the present invention is not changed.

What is claimed is:

1. An image pickup system comprising:
a light source apparatus comprising:
a light source configured to supply illumination light to an object and perform pulse width modulation (PWM) in any duty width; and
a processor; and
an image pickup apparatus provided separately from the light source apparatus, the image pickup apparatus storing data of a numerical value indicating a period in which a light amount control by the PWM is carried out,
wherein the processor is configured to:
read out the data from the image pickup apparatus, and set a numerical value of the data to maximum duty width; and
perform, on the light source, first control for narrowing down a duty width between the maximum duty width and minimum duty width and perform second control for, after the duty width is narrowed down to the minimum duty width by the first control, changing supply timing of the illumination light not to supply the illumination light to the object in a period other than the period in which the light amount control by the PWM is carried out and to supply, in the period in which the light amount control by the PWM is carried out, light having a light amount integral value equal to a light amount integral value supplied in the period other than the period in which the light amount control by the PWM is carried out, and
wherein, in the image pickup apparatus, data representing a value of a driving current to be supplied to the light source after the change of the supply timing of the illumination light and a value of the pulse width is further stored.

2. The image pickup system according to claim 1, wherein the processor is configured to perform third control for controlling amplitude of the driving current supplied to the light source to increase and decrease between a maximum value and a minimum value that can be supplied and further perform the first control when it is necessary to limit a light amount of the illumination light after the third control.

3. A light source apparatus that is connectable to an image pickup apparatus that stores data of a numerical value indicating a period in which a light amount control by pulse width modification is carried out, the light source apparatus comprising:
a light source configured to supply illumination light to an object and perform pulse width modulation (PWM) in any duty width; and
a processor configured to:
read out the data from the image pickup apparatus, and set a numerical value of the data to maximum duty width;
perform, on the light source, first control for narrowing down a duty width between the maximum duty width and minimum duty width and perform second control for, after the duty width is narrowed down to the minimum duty width by the first control, changing supply timing of the illumination light not to supply the illumination light to the object in a period other than the period in which the light amount control by the PWM is carried out and to supply, in the period in which the light amount control by the PWM is carried out, light having a light amount integral value equal to a light amount integral value supplied in the period other than the period in which the light amount control by the PWM is carried out; and read out data representing a value of a driving current to be supplied to the light source after the change of the supply timing of the illumination light and a value of the pulse width, the data being stored in the image pickup apparatus, to set the read-out data as the value of the driving current to be supplied to the light source after the change of the supply timing of the illumination light and the value of the pulse width.

4. An image pickup apparatus that is connectable to a light source apparatus, wherein the light source apparatus comprises:
a light source configured to supply illumination light to an object and perform pulse width modulation (PWM) in any duty width; and
a processor configured to perform, on the light source, first control for narrowing down a duty width between maximum duty width and minimum duty width, and wherein the image pickup apparatus is configured to:
store data of a numerical value indicating a period in which a light amount control by pulse width modification is carried out in an image pickup period of one frame; and
further store data representing a value of a driving current to be supplied to the light source and a value of a pulse width, the data being used after a change of supply timing of the illumination light by a second control performed on the light source by the processor, the second control being for changing the supply timing of the illumination light not to supply the illumination light to the object in a period other than the period in which the light amount control by the PWM is carried out and to supply, in the period in which the light amount control by the PWM is carried out, light having a light amount integral value equal to a light amount integral value supplied in the period other than the period in which the light amount control by the PWM is carried out.

* * * * *